(12) United States Patent
Miles et al.

(10) Patent No.: US 11,833,074 B2
(45) Date of Patent: Dec. 5, 2023

(54) MEN'S GARMENT FOR RECOVERY AFTER UROLOGICAL PROCEDURES, GENITAL SURGERY AND GENITAL INJURY

(71) Applicant: Primetime Ventures, LLC, Indianapolis, IN (US)

(72) Inventors: John F. Miles, Greenwood, IN (US); Thomas Allen Gardner, Indianapolis, IN (US); Matthew Mellon, Carmel, IN (US); John J. Mulcahy, Madison, AL (US)

(73) Assignee: Primetime Ventures, LLC, Indianapolis, IN (US)

( * ) Notice: Subject to any disclaimer, the term of this patent is extended or adjusted under 35 U.S.C. 154(b) by 328 days.

(21) Appl. No.: 17/061,609

(22) Filed: Oct. 2, 2020

(65) Prior Publication Data
US 2021/0100681 A1     Apr. 8, 2021

Related U.S. Application Data

(60) Provisional application No. 62/909,999, filed on Oct. 3, 2019.

(51) Int. Cl.
*A61F 7/02* (2006.01)
*A41B 9/12* (2006.01)
(Continued)

(52) U.S. Cl.
CPC .......... *A61F 5/453* (2013.01); *A41B 9/02* (2013.01); *A41B 9/12* (2013.01); *A41B 9/14* (2013.01);
(Continued)

(58) Field of Classification Search
CPC ............ A41B 9/02; A61F 5/453; A61F 5/451
See application file for complete search history.

(56) References Cited

U.S. PATENT DOCUMENTS 5,405,312 A * 4/1995 Jacobs ............... A41D 13/0568
128/892
5,920,914 A * 7/1999 Dempsey ................. A41B 9/02
2/403

(Continued)

OTHER PUBLICATIONS

International Search Report corresponding to International application No. PCT/US2020/053887 dated Dec. 9, 2020 (14 pages).

*Primary Examiner* — Catharine L Anderson
*Assistant Examiner* — Arjuna P Chatrathi
(74) *Attorney, Agent, or Firm* — Maginot, Moore & Beck LLP

(57) ABSTRACT

A garment is provided to be worn post-surgery during recovery from urological surgical procedure. The garment is in the form of men's underwear or brief, with features provided to assist in recovery and comfort of the user. The garment includes a center flap that can be opened to provide access to a center pocket that is aligned with the user's crotch. The center pocket contains a moldable body that can be molded to a particular shape to support and hold the user's penis in a pre-determined orientation to facilitate the recovery process. The flap also includes a pocket that can contain a heating/cooling pack that is arranged to apply heat/cooling to the surgical site. The garment is also configured to accept and support a medical drainage tube to drain the surgical wound, and a drainage pump as needed.

13 Claims, 2 Drawing Sheets

(51) Int. Cl.
*A41B 9/02* (2006.01)
*A41B 9/14* (2006.01)
*A61F 5/453* (2006.01)
*A61F 5/44* (2006.01)

(52) U.S. Cl.
CPC .............. *A61F 5/4404* (2013.01); *A61F 7/02* (2013.01); *A61F 2007/0238* (2013.01)

(56) References Cited

U.S. PATENT DOCUMENTS

| | | | | |
|---|---|---|---|---|
| 5,984,910 | A * | 11/1999 | Berke | A41B 9/023 |
| | | | | 128/854 |
| 6,412,119 | B1 * | 7/2002 | Robles | A41B 9/026 |
| | | | | 2/400 |
| 8,702,667 | B1 * | 4/2014 | Johnson | A61F 13/471 |
| | | | | 604/385.03 |
| 2006/0101558 | A1 * | 5/2006 | Coleman | A61F 13/8405 |
| | | | | 2/400 |
| 2006/0191059 | A1 * | 8/2006 | Smith | A41B 9/005 |
| | | | | 2/400 |
| 2013/0158635 | A1 * | 6/2013 | Federico | A61F 7/10 |
| | | | | 607/108 |
| 2014/0275906 | A1 * | 9/2014 | Hackenburg | A41D 13/1281 |
| | | | | 2/109 |
| 2016/0157531 | A1 * | 6/2016 | Fisher | A41D 1/088 |
| | | | | 2/403 |
| 2016/0206021 | A1 * | 7/2016 | Gawrys | A61F 5/30 |
| 2017/0099887 | A1 * | 4/2017 | Boillat-Macon | A41D 13/1254 |
| 2017/0135875 | A1 * | 5/2017 | Johnson | A61F 13/4906 |
| 2017/0246338 | A1 * | 8/2017 | Taylor | H05B 3/34 |
| 2019/0274374 | A1 * | 9/2019 | Marconi | A41B 9/026 |

* cited by examiner

MEN'S GARMENT FOR RECOVERY AFTER UROLOGICAL PROCEDURES, GENITAL SURGERY AND GENITAL INJURY

PRIORITY CLAIM

This application is a utility filing from and claims priority to U.S. Provisional Application No. 62/909,999, filed on Oct. 3, 2020, the entire disclosure of which is incorporated herein by reference.

BACKGROUND

Urinary and genital health is not a topic that many men are comfortable discussing. The facts are that most of the male population will receive some form of urological medical treatment and/or surgery for male urinary and genital related issues.

Aging increases the likelihood for the need for urinary related medical treatments and procedures. Many of these procedures can be quite serious, even life endangering, often going beyond just treatments requiring recovery from post-urinary medical procedures and post-surgery. In many instances, home recovery will be required under physicians care, ranging from a few days to several weeks. Examples of post male urinary treatments, procedures and surgeries that require extended post-procedure recovery periods are:

Groin and/or urinary trauma or injury.
Urinary out-patient medical actions such as a vasectomy.
Urology-related cancer surgery procedures and recovery.
Male implant surgical procedures and recovery.
Most urological procedures that requires post treatment recovery Treatment for testicular cancers is perhaps the most common of the urology-related cancer surgeries. The surgery, called a radical inguinal orchiectomy, involves removal of the affected testicle(s) through an incision in the abdomen just above the pubic area. The cancerous tumor and spermatic cord are removed along with the testicle. In many cases, a testicular prosthesis is implanted in the scrotum to replace the missing testicle and maintain the same outward appearance of the scrotum. The conventional post treatment recovery protocol for this type of surgery, as well as for the other procedures identified above, includes icing of the treated injured groin or post surgical effected area while resting through recovery. Many times, urologists recommend that the penis be placed in a certain position during recovery for the best possible post-treatment outcome.

The typical post-procedure recovery recommendation is simply to wear close-fitting underwear, such as briefs or Y-fronts, rather than boxer shorts. However, these garments do not provide sufficient immobilization and support of the scrotum, testicles and/or penis, and do not provide adequate protection for this sensitive region made much more sensitive from the urological procedure or surgery.

Conventional icing applications to the affected region can be awkward and fraught with difficulties in trying to maximize the recovery icing treatments. In the typical case, the patient is advised to use bags of frozen vegetable or homemade ice bags to apply to the effected targeted area. The difficulties associated with this approach are evident.

There are also issues with the conventional recovery protocol with respect to personal mobility, resting and sleeping, particularly with respect to protection and positioning of genitalia during recovery after urinary procedures. Most existing treatment and method recommendations do not efficiently provide support that allows for comfortable mobilization, support protection and proper in-place positioning of the genitalia as recommended by the urologist. The difficulties can be accentuated during patient treatments while sleeping.

SUMMARY OF THE DISCLOSURE

A garment is provided to be worn by men recovering from a urological procedure, such as surgery. The garment is in the form of men's underwear or brief, and includes a leg portion including two legs configured for receiving the legs of the user when the garment is worn by a user, and an integral abdomen portion having an adjustable waistband configured to be worn on the abdomen of the user. The abdomen portion defines a center opening with a center panel spanning the center opening. The center panel includes an inner pocket accessible through the center opening. A moldable body is permanently or removably disposed within the inner pocket in alignment with the penis of the user when the garment is worn. The moldable body is configured to be molded to support the user's penis in a pre-determined orientation within the garment, such as vertical to keep the penis clear of the surgical wound.

The garment further includes a flap that is attached to the garment at a hinge line between the two legs. The flap is movable from a closed position in which the flap covers the center opening, to an open position in which the center opening is accessible from outside the garment. The flap can also include a pocket for containing a heating/cooling pack, arranged to be inside the garment when the flap is closed. The flap thus allows the user to manipulate, and/or insert and remove, the moldable body as needed, and to insert or remove a heating/cooling pack as needed. The garment is also configured to accept a medical drainage tube for draining the surgical wound. A drainage pump can be supported within a pocket on one or both of the legs of the garment.

The flap is closed with a releasable attachment feature between the flap and the abdomen portion of the garment. The attachment feature at the upper end of the flap can include mating attachment patches adjacent the waistband of the garment, such as hook-and-loop fasteners. The flap includes a pair of side wings between the waistband and the crotch of the garment that also includes mating attachment patches, such as hook-and-loop fasteners. The attachment feature allows the flap to be comfortably engaged to the abdomen portion of the garment when the moldable body and heating/cooling pack are in place.

DETAILED DESCRIPTION

Figure 1:
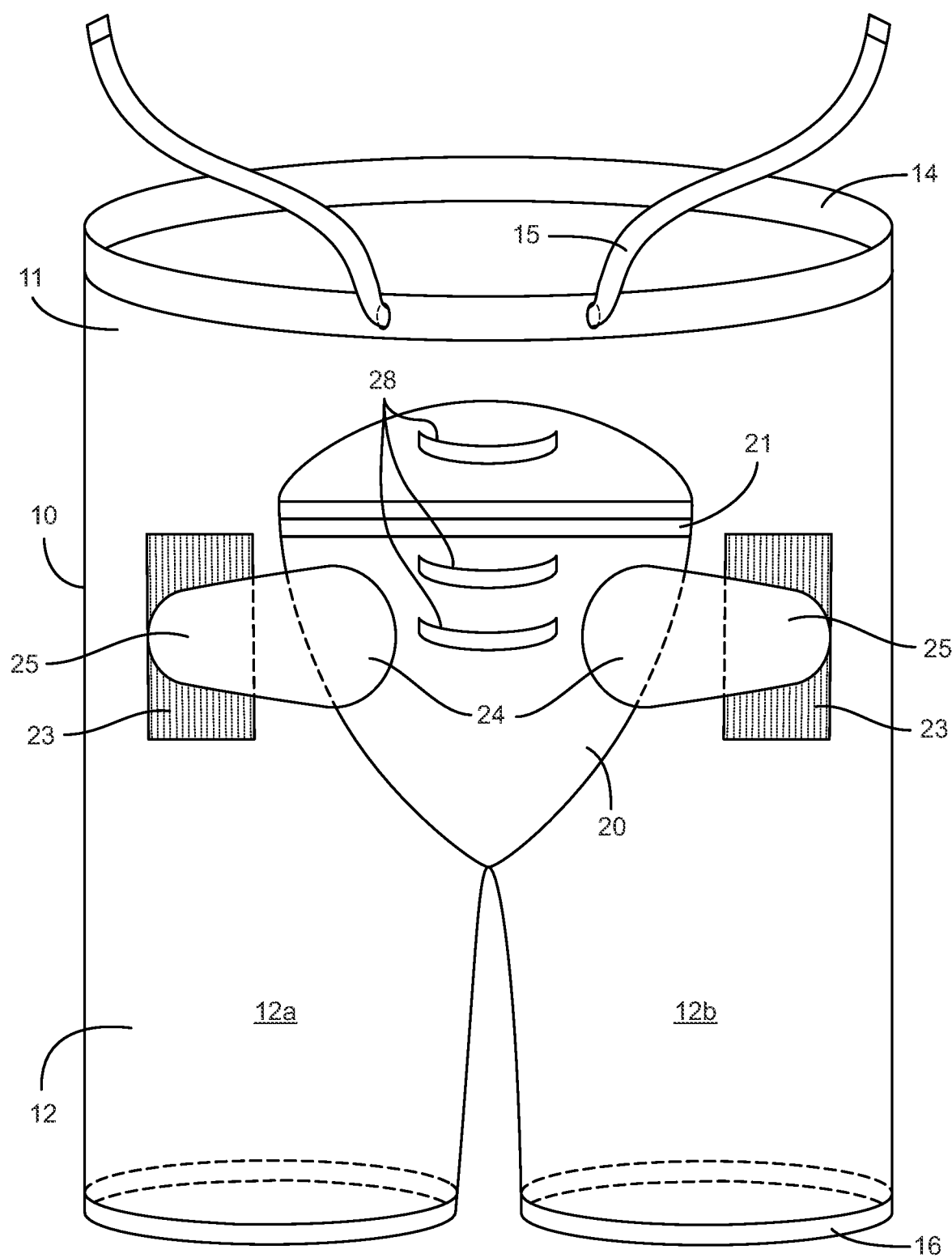
FIG. 1 is a front view of a garment according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains A garment 10 shown in FIG. 1 is configured to protect the scrotum and penile region following a urological region injury, surgery, such as radical inguinal orchiectomy, or urological procedure to facilitate pain management and recovery. The garment is configured to be worn like men's underwear or gym shorts, so it includes an abdomen portion 11 that is open at the waistband 14 and a leg portion 12 with a pair of legs 12a, 12b that define leg openings. The waistband 14 can be elastic, but it is desirable that the waist portion not be too difficult for the wearer to step into and pull up to his waist. Thus, the waistband can be only loosely elastic and can be provided with a drawstring 15 to tighten the waistband about the waist of the convalescing person. The legs 12a, 12b can also be provided with an elastic band 16 at the leg openings, but like the waistband it is preferable that the elastic band 16 not be too tight to complicate the process of pulling the garment on.

The garment can be made of a breathable and comfortable material, such as a cotton-polyester blend known in the garment industry. Thus far, the garment 10 is similar to conventional form-fit boxer underwear, although the waistband and leg openings are preferably not as tight on the wearer as typical form-fit boxers, similar to how gym shorts might fit in the waist and legs. The material is also preferably not as form-fitting as the conventional boxer brief. In a further deviation from the conventional boxer brief, the garment 10 includes a plastic-lined pocket 20 at the crotch of the garment. The plastic-lining is on the inside of the pocket because the pocket is configured to house an icing insert or cooling pad. The cold icing insert or cooling pad (not shown) can be placed into the pocket through a sealable opening 21. In one embodiment, the sealable opening can be an interlocking seal, such as the ZIPLOC® seal used on sandwich and freezer bags. The cooling insert can be of any known type, ranging from a cooling pad to an inserted bar or beads kept frozen until needed, to a bag of crushed ice cubes. The pocket 20 can be configured to expand outwardly from the garment to accept the frozen icing insert different sizes of cooling pads depending on the cooling requirements.

In one embodiment, the pocket can be affixed to the fabric of the garment 10 in a conventional manner. In another embodiment, the pocket 20 is a separate component from the remainder of the garment so that it can be removed when it is not needed. Thus, in this embodiment, the pocket is in the form of a free-standing pouch that is removably attached to the garment. In either embodiment, it is contemplated that the pocket or pouch containing the icing insert can be form-fitted to the user's genital anatomy. This form-fitting feature allows the patient to ensure that the cooling effect is applied where it is needed and to ensure that the icing insert is in close proximity to the region in need of the cooling effect of the icing insert. The abdomen portion 11 of the garment can include a patch 23 aligned with each leg of the garment. The patch is configured to releasably connect a positioning strap 25, which strap is also releasably connected to a similar patch 24 on the pocket 20. In another embodiment, the positioning strap 25 can be directly affixed to the abdomen portion 11 of the garment. In one specific embodiment, the patches 23, 24 and strap 25 can be configured with a hook-and-loop fastening component, such as a VELCRO™ fastener. The strap 25 can be engaged to the respective patches 23 and/or 24 with the amount of overlap of the strap to the patches being adjustable to suit the comfort of the person wearing the garment 10.

It can be appreciated that in one version of the garment 10, a sealable ice pocket is integrated into the garment, either as a separate attachment or as an integral part of the garment. In one aspect of disclosure, the ice pocket can incorporate an adjustable foam guide that will allow for specific positioning of the penis. This version can be referred to as the awake or day time treatment version that is worn by the patient while awake. In another version, the garment does not include the sealable ice pocket, but still includes an adjustable foam guide configured for proper positioning of the penis. This version is particularly suitable for sleeping and non-icing mobility time. The garment still supports the penis in a preferred position for recovery, but is not burdened with the icing insert that might inhibit mobility or frustrate the patient's ability to sleep. It is thus contemplated that two separate garments may be provided to the recovering patient—one with the icing insert pocket and one without. Alternatively, as described above, the icing insert pocket can be configured for removal from the garment as needed.

One important aspect in the recovery from the surgery or procedures is to support and restrain the penis in a particular attitude directed by the treating urologist. In particular, it is preferable for the penis to be oriented vertically to avoid contact with the wound, and for the penis to be restrained to prevent movement of the genital region that might compromise the sutures used to close the wound. Consequently, in one aspect of the present garment, the abdomen portion 11 can include bendable strips 28 that extend laterally across the center front of the garment. The strips 28 are preferably integrated into a moldable padded penile support and positioning pocket area in the garment. In lieu of the strips, a close-fitting pocket can be formed from a bendable or moldable material, either as a separate component or integrated into the garment fabric. The strips or moldable support pocket is constructed of washable materials, and may be sewn into the garment or removable from the garment during washing. The strips 28 or moldable pocket are formed of a material can be bent or formed into a particular configuration and hold that configuration. In one specific embodiment, the strips 28 can be formed of same material as the nose clips for conventional breathing masks, namely aluminum. The person wearing the garment can bend the strips to engage the penis and hold the penis in a generally vertical orientation but in the position instructed by the Urologist adjusting the amount of bend for comfort. One or more strips 28 may be provided in the garment 10. In the alternative, the moldable pocket can be incorporated in a manner that allows the patient to mold the cup while wearing the garment to ensure a comfortable and functional fit.

Figure 4:
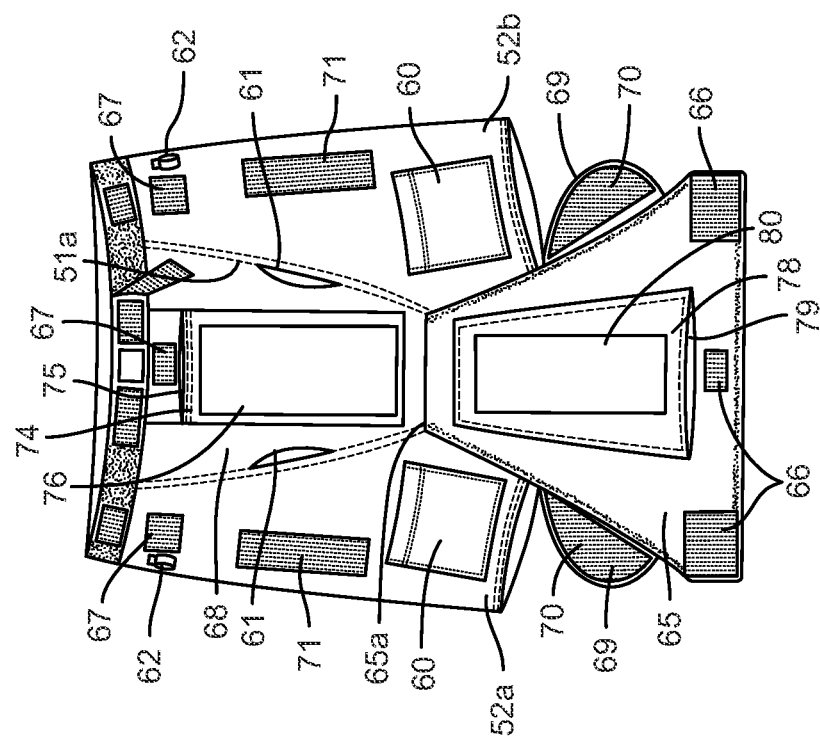
FIG. 4 is a front view of the garment shown in FIG. 2, depicted with a front flap opened.
Figure 2:
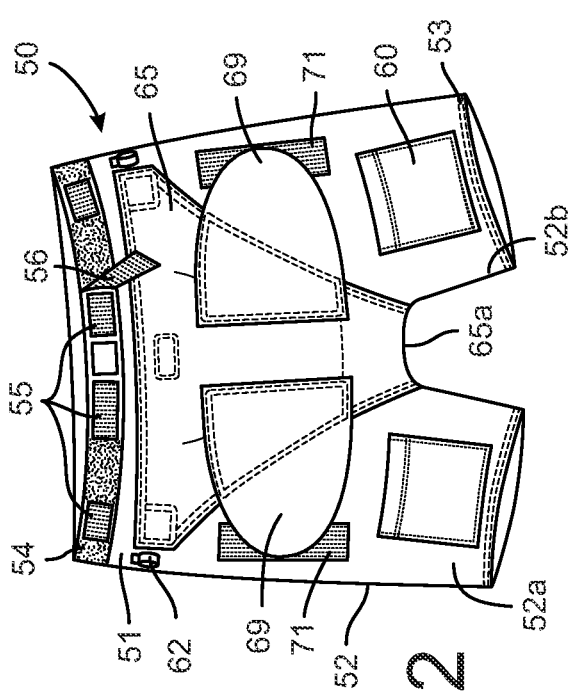
FIG. 2 is a front view of a garment according to a further embodiment of the present disclosure.
Figure 3:
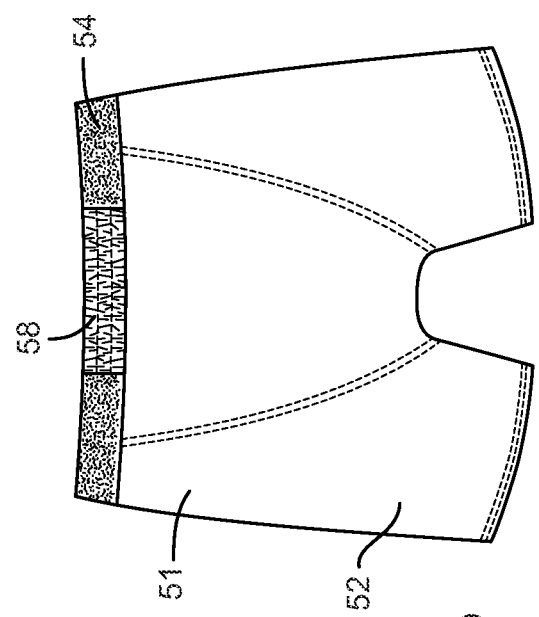
FIG. 3 is a back view of the garment shown in FIG. 2.

A garment 50 according to another embodiment of the present disclosure is shown in FIGS. 2-4. Like the garment 10, the garment 50 can be made of a breathable and comfortable material, such as a cotton-polyester blend known in the garment industry. The garment 50 includes an abdomen portion 51 that defines an opening for receiving the wearer's abdomen, and a leg portion 52 that includes two legs 52a, 52b, each defining an opening for receiving the wearer's leg. Like the legs 12a, 12b, the legs 52a, 52b can have an elastic band 53 at the leg openings.

The abdomen portion 51 includes a waistband 54 that encircles the wearer's waist to hold the garment on the body. The waistband includes adjustment patches 55 that can adjustably engage an adjustment strap 56 to conform the circumference of the waistband to the circumference of the wearer's waist. The patches 55 and strap 56 can be configured with a hook-and-loop fastening component, such as VELCRO™ fasteners for easy removable engagement of the adjustment components. A single strap 56 can be provided, as shown in FIG. 2, or left and right straps can be provided to adjust the waistband on the user's waist. As shown in FIG. 3, the back of the waistband 54 can include an elastic portion that can flex to tension the waistband once the wearer has adjusted the strap 56 on the patches 55.

Recovery from some surgeries may involve drainage tubes at the surgical site to drain the wound. To facilitate introduction of drainage tubes, the abdomen portion 51 of the garment can include slits 61 adjacent each leg 52a, 52b and more particularly adjacent the surgical wound of the wearer. A drainage tube (not show) can be introduced to either, or both, slits 61 and supported by a corresponding loop 62 for connection to a collection receptacle. The loop 62 can be in the form of a closed fabric or elastic loop, or can be a resilient clip adapted for retaining flexible medical tubing. A drainage pump is sometimes necessary, so the garment includes a pocket 60 on each leg that can be connected to the drainage tube passing through a corresponding slit 61. The pocket 60 can be formed of the same material as the remainder of the garment and can include a closable opening for containing a conventional drainage pump. Alternatively, the pocket can be formed of a mesh material to dissipate any heat generated by the pump. The pocket 60 can be lined to reduce heat transmission to the wearer's leg when the pump is operating.

In one important feature, the garment 50 includes a center flap 65 that can be opened and closed over a center panel 68 that is disposed over the groin and surgical site of the wearer. The center panel 68 can define the slits 61. The flap 65 is a generally trapezoidal-shaped panel that is sewn to the garment 51 at a hinge line 65a at the bottom of the flap so that the flap can be pivoted about the hinge line between a closed position, as shown in FIG. 2, and an open position, as shown in FIG. 4. The hinge line 65a is preferably at the crotch of the garment (i.e., between the legs 52a, 52b) so that the flap can extend from the groin to the lower abdomen of the user. The abdomen portion 51 defines an opening 51a through which the center panel 68 is accessible and which is covered by the center flap 65. The center panel 68 and the opening 51a are generally trapezoidal-shaped, like the center flap, but slightly smaller in perimeter dimension than the flap so that the flap can overlap the garment at the sides and upper end of the center opening. The center flap and abdomen portion include an attachment feature therebetween that allows the center flap to be removably attached to the abdomen portion to close the center opening. Thus, in one embodiment, the center flap 65 includes attachment patches 66 at the upper end of the flap that can be releasably engaged to attachment patches 67 at the upper portion of the abdomen portion 51 adjacent the waistband. The center flap 65 includes side wings 69 that are situated between the hinge line 65a and the attachment patches 66 at the upper end of the flap. The side wings also include attachment patches 70 for releasable engagement to attachment patches 71 on the abdomen portion of the garment. The attachment patches can be configured as components that can be readily engaged and disengaged, such as a hook-and-loop fastening components (i.e., VELCRO™ fasteners).

The center flap 65 can be opened, as shown in FIG. 4, to provide access to an inner pocket 74 sewn to the center panel 68. The inner pocket contains a moldable body 76 that can be either sewn into the pocket or inserted into the pocket through an opening 75. The moldable body 76 provides substantially the same function as the bendable strips 28 described above. In particular, the moldable body 76 can be formed by the user to mold around the penis in a desired orientation, such as the vertical orientation to keep the penis clear of the surgical wounds. The body 76 can further hold the penis in the position until the garment or moldable body is removed. The moldable body 76 can constitute a sealed pouch containing a moldable resin or plastic that is capable of being molded to a desired shape and of holding that shape until re-molded. For instance, a moldable plastic, such as a PVC-ethylene copolymer or a polyurethane plastic, can be molded after heating and then holds the molded shape upon cooling. The body can be in the form of a generally rectangular panel with sufficient surface area to partially enshroud the penis inside the garment 50. The panel can have a minimal thickness, such as ⅛ inch, provided the moldable material can retain the desired shape during use. It is contemplated that the user can access the moldable body 76 within the inner pocket 74 when the flap 65 is open, as shown in FIG. 4. Once the body has been molded into shape, the flap can be closed, as shown in FIG. 2. The inside wall of the inner pocket 74, or more particularly the surface of the pocket in direct contact with the user's body, can be formed of a mesh material, rather than the fabric of the remainder of the garment 50.

The flap 65 includes an outer pocket 78 on an inside surface of the flap facing the inner pocket 74. The outer pocket includes an opening 79 to receive a heating/cooling pack 80. The pack 80 is preferably flexible so that it can be at least partially formed to the outer shape of the moldable body 76. The inner wall of the outer pocket 78 can be formed of a mesh material so that the material of the pocket does not inhibit the transmission of the heat or cold from the pack 80 to the body of the user. The outer wall of the inner pocket 74 can also be formed of a mesh material for the same reason. The flap 65 can be formed of the same fabric as the abdomen portion and leg portion of the garment, or can be formed of a more insulating material to help retain the heat or cold generated by the heating/cooling pack 80.

The flap 65 allows the user to tailor the garment 50 to his needs. The inner pocket 74 is readily accessible when the flap 65 is open to insert, remove or adjust the moldable body 76 within the pocket. It is contemplated that the moldable body would be in place when the user is sleeping but not necessarily when the user is up and about. Similarly, it is contemplated that the user may not want heat or cooling treatment when sleeping, so the heating/cooling pack 80 can be easily removed from the flap 65. As needed, the inner pocket 74 can house an incontinence pad in lieu of or in addition to the moldable body 76. The attachment patches 66/67/70/71 simplify the opening and closing of the flap 65 and allow the user to adjust the tightness of the flap on the front of the garment 50. The garment also accommodates a drainage tube that can be easily passed through a slit 61 and between the flap 65 and the abdomen portion 51, even when the flap is closed. The drainage tube can then pass to a pump within the pocket 60 or to a loop 62 on the garment.

The present disclosure should be considered as illustrative and not restrictive in character. It is understood that only certain embodiments have been presented and that all changes, modifications and further applications that come within the spirit of the disclosure are desired to be protected.

What is claimed is:

1. A garment to be worn post-surgery, comprising:
   a leg portion including two legs configured for receiving the legs of the user when the garment is worn by a user;

an abdomen portion integral with said leg portion and having a waistband configured to be worn on the abdomen of the user, the abdomen portion defining a center opening with a center panel spanning the center opening, the center panel including an inner pocket accessible through said center opening;

a moldable body disposed within said inner pocket in alignment with the penis of the user when the garment is worn, wherein the moldable body is configured to be molded within the inner pocket at any time when the garment is worn by the user to support the user's penis in a pre-determined orientation within the garment; and a flap attached to the abdomen portion at a hinge line between the two legs so that the flap is movable from a closed position in which the flap covers said center opening, preventing access to said inner pocket through said center opening, to an open position in which, when the garment is worn by the user, said inner pocket is accessible through said center opening from outside the garment, wherein said inner pocket is only accessible when the flap is in said open position.

2. The garment of claim 1, wherein said moldable body is formed of a moldable resin or plastic that can be molded to a shape and retain that shape until molded again by the user.

3. The garment of claim 1, wherein said flap includes an outer pocket on an inner surface of the pocket facing the center panel when the flap is in the closed position.

4. The garment of claim 3, further comprising a heating or cooling pack contained within said outer pocket.

5. The garment of claim 1, wherein said abdomen portion defines one or more slits accessible through said center opening, said one or more slits sized to receive a medical drainage tube extending therethrough.

6. The garment of claim 5, further comprising one or more loops fastened to the outside of the abdomen portion of the garment, said one or more loops sized to receive a medical drainage tube extending therethrough.

7. The garment of claim 5, wherein at least one of said legs of the leg portion includes a pocket sized to receive a drainage pump connectable to the medical drainage tube.

8. The garment of claim 1, further comprising an attachment feature between said abdomen portion and said flap configured to releasably attach said flap to said abdomen portion when the flap is in said closed position.

9. The garment of claim 8, wherein said attachment feature includes first upper attachment patches on said abdomen portion adjacent said waistband and corresponding second upper attachment patches on said flap configured and arranged to align with and engage said first upper attachment patches when the flap is in the closed position.

10. The garment of claim 9, wherein:

said flap includes a pair of side wings, each wing extending from each opposite side of said flap and arranged between said hinge line and said second upper attachment patches of said flap; and said attachment feature includes third attachment patches on each of said pair of side wings and fourth attachment patches on said abdomen portion configured and arranged to engage the third attachment patches on said pair of side wings when said flap is in the closed position.

11. The garment of claim 1, wherein said abdomen portion includes an adjustable waistband configured to be tightened around the waist of the user when the garment is worn.

12. The garment of claim 11, wherein said waistband includes a drawstring for tightening around the waist of the user.

13. The garment of claim 11, wherein said waistband includes one or more patches and one or more straps, with attachment elements between the one or more patches and the one or more straps configured for adjustable and removable engagement between the one or more straps and the one or more patches at adjustable positions around the perimeter of the waistband.

* * * * *